US009533052B2

(12) United States Patent
Matsuda et al.

(10) Patent No.: US 9,533,052 B2
(45) Date of Patent: Jan. 3, 2017

(54) AQUEOUS OPHTHALMIC SUSPENSION OF CRYSTALLINE REBAMIPIDE

(71) Applicant: OTSUKA PHARMACEUTICAL CO., LTD., Chiyoda-ku, Tokyo (JP)

(72) Inventors: Takakuni Matsuda, Tokushima-ken (JP); Shogo Hiraoka, Tokushima-ken (JP); Yuso Tomohira, Tokushima (JP); Shinichi Ishikawa, Komatsushima (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/887,222

(22) Filed: Oct. 19, 2015

(65) Prior Publication Data
US 2016/0101183 A1    Apr. 14, 2016

Related U.S. Application Data

(62) Division of application No. 11/667,313, filed as application No. PCT/JP2005/021178 on Nov. 11, 2005, now Pat. No. 9,211,254.

(30) Foreign Application Priority Data

Nov. 15, 2004 (JP) ................. 2004-330140

(51) Int. Cl.
| A61K 31/47 | (2006.01) |
| A61K 47/38 | (2006.01) |
| A61K 9/00 | (2006.01) |
| A61K 9/10 | (2006.01) |
| A61K 31/4704 | (2006.01) |
| A61K 47/10 | (2006.01) |
| A61K 47/26 | (2006.01) |
| A61K 47/32 | (2006.01) |

(52) U.S. Cl.
CPC ............ *A61K 47/38* (2013.01); *A61K 9/0048* (2013.01); *A61K 9/10* (2013.01); *A61K 31/4704* (2013.01); *A61K 47/10* (2013.01); *A61K 47/26* (2013.01); *A61K 47/32* (2013.01)

(58) Field of Classification Search
None
See application file for complete search history.

(56) References Cited

U.S. PATENT DOCUMENTS

| 5,366,985 A | 11/1994 | Nakayama et al. |
| 5,560,932 A | 10/1996 | Bagchi et al. |
| 5,662,883 A | 9/1997 | Bagchi et al. |
| 5,665,331 A | 9/1997 | Bagchi et al. |
| 5,716,642 A | 2/1998 | Bagchi et al. |
| 6,060,486 A * | 5/2000 | Urashima .......... A61K 31/4704 514/319 |
| 6,517,853 B1 | 2/2003 | George et al. |
| 2004/0161407 A1 | 8/2004 | Kimura et al. |

FOREIGN PATENT DOCUMENTS

| EP | 0 531 529 A1 | 3/1993 |
| EP | 0 995 435 A1 | 4/2000 |
| JP | 50-121414 | 9/1975 |
| JP | 55-139319 | 10/1980 |
| JP | 09301866 | 11/1997 |
| WO | WO 97/13515 | 4/1997 |

OTHER PUBLICATIONS

Sano, A. et al., "Particle Design of Tolbutamide in the Presence of Soluble Polymer or Surfactant by the Spherical Crystallization Technique: Improvement of Dissolution Rate," Journal of Pharmaceutical Sciences, vol. 76, No. 6, Jun. 1987, 471-474.
Beom Soo Shin et al. (Drug Dev Indust Pharmacy 30:869-876, 2004).
International Preliminary Report on Patentability for PCT/JP2005/021178 issued May 15, 2007.
International Search Report for PCT/JP2005/021178 mailed Jan. 24, 2006.
Supplementary European Search Report for EP Application No. 05 80 6737 dated Jul. 9, 2012.
Urashima, H. et al., "OPC-12759 Ophthalmic Suspension Increases the Ocular Mucin of Rabbits," Investigative Ophthalmology & Visual Science, Association for Research in Vision and Ophthalmology, US, No. Suppl., Jan. 1, 2002, p. Abstract, 49, XP 009160542, ISSN: 0146-0404.
Yoshiyuki Hirakawa et al., "Studies on Development of the Ultrafine Size Reduction Method of Slightly Soluble Medicinal Crystals. I. Evaluation of Size Reduction Effect for Oxolinic Acid by the Polycarbonate Membrane Filtration," Yakugaku Zasshi, vol. 102, No. 10. (1982) pp. 951-959.
Yoshiyuki Hirakawa et al., "Studies on Development of the Ultrafine Size Reduction Method of Slightly Soluble Medicinal Crystals. II. Various Factors Affecting the Ultra-fine Size reduction of Oxolinic Acid Crystal," Yakugaku Zasshi, vol. 103, No. 6, (1983), pp. 690-695.
Yoshiyuki Hirakawa et al., "Studies on Development of the Ultrafine Size Reduction Method of Slightly Soluble Medicinal Crystals. III. The Inference of Origin for Ultra-fine Size Reduction of Oxolinic Acid Crystal," Yakugaku Zasshi, vol. 103, No. 11, (1983), pp. 1215-1218.

(Continued)

*Primary Examiner* — Craig Ricci
(74) *Attorney, Agent, or Firm* — Finnegan, Henderson, Farabow, Garrett & Dunner, L.L.P.

(57) ABSTRACT

The invention provides an ophthalmic product containing rebamipide, which has a transparency enough to be agreeable feeling on using it and has neutral so weakly acidic pH not to injury of the keratoconjunctiva of a patient suffering from dry eye. An aqueous suspension of crystalline rebamipide which has an improved transparency is provided by adding an aqueous solution of rebamipide dissolved by a base such as sodium hydroxide or an aqueous solution of a salt of rebamipide to an aqueous acidic solution such as hydrochloric acid containing at least one of the compounds selected from water-soluble polymers and surfactants, and mixing them.

8 Claims, 3 Drawing Sheets

(56) References Cited

OTHER PUBLICATIONS

Yoshiyuki Hirakawa et al., "Studies on Development of the Ultra-fine Size Reduction Method of Slightly Soluble Medicinal Crystals. IV. Enhanced Bioavailability of Oxolinic Acid by Ultra-fine Size Reduction," Yakugaku Zasshi, vol. 103, No. 11, (1983), pp. 1190-1194.
Yoshiyuki Hirakawa et al., "Studies on Development of the Ultra-fine Size Reduction Method of Slightly Soluble Medicinal Crystals. V. Size Reduction of Phenytoin and Phenobarbjtal," Yakugaku Zasshi, vol. 104, No. 1, (1984), pp. 91-96.

\* cited by examiner

200; 200000

AQUEOUS OPHTHALMIC SUSPENSION OF CRYSTALLINE REBAMIPIDE

This is a division of application Ser. No. 11/667,313, §371(c) date of May 9, 2007, which is the National Stage of PCT/JP05/21178, filed Nov. 11, 2005 and claims foreign priority to JP 2004-330140, filed Nov. 15, 2004, all of which are incorporated herein by reference.

TECHNICAL FIELD

The invention relates to an aqueous ophthalmic suspension product which does not need to be re-dispersed and exhibits a remarkable transparency and stability, comprising rebamipide [Chemical name: 2-(4-chlorobenzoyl-amino)-3-(2-quinolon-4-yl)propionic acid] as an active ingredient, and a method for manufacturing it.

BACKGROUND ART

Rebamipide or the salt thereof, which is an active ingredient in the aqueous suspension of the invention, is known as a useful antiulcer drug. In addition, rebamipide has an increasing action of goblet cell density in eye, an increasing action of mucus in eye, and an increasing action of lacrimal fluid, and has been already known as ah agent for treating dry eye, i.e. dry eye syndrome (JP-A-9-301866).

Sugimoto and Hirakawa reported on a method for providing a fine-grained crystal, which comprises neutralizing a water-soluble salt given from an insoluble acid compound and a base with an acid in the presence of a polymer compound and/or a surfactant (JP-A-50-121414). In addition, Hirakawa et al. detailedly reported on a micronization of oxolinic acid through the above process [YAKUGAKU ZASSHI 102(10) 951-959 (1982), ibidem 103(6) 690-695 (1983), ibidem 103(11) 1215-1218 (1983), and ibidem 103(12) 1190-1194 (1983)]. Furthermore, Hirakawa et al. reported that they managed to micronize phenytoin and phenobarbital to only at maximum 3 to 4 μm of the average particle size through the above process [YAKUGAKU ZASSHI 104(1) 91-96 (1984)]. Sato et al. also reported on a method for micronizing an insoluble compound which is soluble with acid or base, by means of neutralization (JP-A-55-139319).

Pranab Bagchi et al. reported on a method for preparing a nanoparticle, which comprises dissolving a pharmaceutical compound with a base and neutralizing it with an acid in the presence of s surface-modifylng agent and a surface-activating agent (U.S. Pat. Nos. 5,560,932, 5,662,883, 5,665,331, and 5,716,642).

As mentioned above, the method for preparing a fine-grained crystal, which comprises neutralizing a water-soluble salt given from an acid compound and a base with an acid in the presence of a polymer compound and/or a surfactant, is a known prior art. However, as shown in the above examples of phenytoin and phenobarbital, the micronized size may largely depend on the type of compound, so it is hard to predict it. Besides, there were not any similar reports about rebamipide until now. In general, even if the mircronization is led to sub-micron level, the suspension will exhibit a white milky feature; accordingly there has not been any report about a method to prepare a solution having a high transparency suitable for ophthalmic use as disclosed in the invention. Further, there has not been any report about a method to prepare a suspension having a surprisingly high transparency by the way that the pH of the suspension prepared by crystallization is adjusted, to 3-7 and then the mixture is stirred and/or dispersed. Furthermore, there has not been any report about a method to prepare a suspension having a markedly more improved transparency by additional dialyzing process. Additionally, there has not been any report about a method to prepare a needle crystal of rebamipide having a ratio between the long gage length and the short gage length is not less than 4, which exhibit a specific transparency.

DISCLOSURE OF INVENTION

Rebamipide is soluble in a basic aqueous solution, but the solubility of rebamipide in a neutral solution is too low. On the other hand, a high-pH eye drop is not suitable for a disorder which involves injury of keratoconjunctiva, e.g. dry eye. Additionally, even in case of a basic solution containing rebamipide, the crystal of rebamipide may be occasionally deposited with ease and hence it is thought that the development of the aqueous ophthalmic product of rebamipide is difficult.

JP-A-9-301866 discloses a neutral aqueous suspension containing rebamipide, but the suspension may form a precipitate layer when standing for a long period. Therefore, the suspension needs to be shaken well in order to be re-dispersed. In addition, such suspension product may be thought to have some demerits, for example suffering from blurred vision and making some white spots on the cloths when spilling the suspension, because the suspension product is a white ophthalmic suspension.

Therefore, it has been desired to develop an ophthalmic product containing rebamipide, which is unnecessary to be re-dispersed, has a transparency enough to be agreeable feeling on using, and exhibits neutral to weakly acidic pH not to injure the keratoconjunctiva of a patient suffering from dry eye.

The present inventors have extensively studied to reach the above object and then have found that an aqueous ophthalmic suspension containing rebamipide which exhibits a preferable re-dispersibility and an improved transparency contrary to his expectation can be prepared by mixing at least one of the compounds selected from water-soluble polymers and surfactants, an aqueous acidic solution, and an aqueous solution containing a water-soluble salt of rebamipide (with exposure to ultrasonic wave). Based upon the new findings, the present invention has been completed.

The invention relates to an aqueous suspension containing crystalline rebamipide suitable for eye drop, which comprises a mixture of at least one of the compounds selected from water-soluble polymers and surfactants, an aqueous acidic solution; and an aqueous solution containing a water-soluble salt of rebamipide.

The invention, also relates to the following;

the above aqueous suspension containing crystalline rebamipide wherein the pH value is adjusted to the range of 5-7 with a base;

the aqueous ophthalmic suspension containing crystalline rebamipide which is producible by adding a base to the above aqueous suspension to adjust pH to 3-7, dispersing and/or dialyzing the mixture, and then adjusting pH to 5-7 and adjusting the concentration of rebamipide to 0.5-5% (w/v);

the sterile aqueous ophthalmic suspension containing crystalline rebamipide which is producible by adding a base to the above aqueous suspension to adjust pH to 3-7, dispersing and/or dialyzing the mixture, then adjusting pH to 5-7 and adjusting the concentration of rebamipide to 0.5-5% (w/v), and filtrating the mixture for sterilization;

the above aqueous ophthalmic suspension containing crystalline rebamipide wherein the concentration of rebamipide in the suspension concentrated by the dialysis is adjusted to 0.5-5% (w/v) with purified water;

the above aqueous suspension containing crystalline rebamipide wherein the aqueous suspension of crystalline rebamipide has a transmission factor at 640 nm of not less than 20%; and the above aqueous ophthalmic suspension containing crystalline rebamipide wherein the shape of the crystalline rebamipide is a regular needle crystal having a long gage length of less than 1000 nm and a short gage length, of less than 60 nm, provided that the ratio between the long gage length and the short gage length is not less than 4.

Furthermore, the invention relates to a method for preparing an aqueous suspension of crystalline rebamipide, comprising mixing at least one of the compounds selected from water-soluble polymers and surfactants, an aqueous acidic solution, and an aqueous solution containing a water-soluble salt of rebamipide;

a method for preparing an aqueous ophthalmic suspension containing crystalline rebamipide, comprising adding a base to the aqueous suspension prepared by the above method to adjust pH to 3-7, dispersing and/or dialysing the mixture, and then adjusting pH to 5-7 and adjusting the concentration of rebamipide to 0.5-5% (w/v); and a method for preparing a sterile aqueous ophthalmic suspension containing crystalline rebamipide, comprising adding a base, to the aqueous suspension prepared by the above method to adjust pH to 3-7, dispersing and/or dialyzing the mixture, then adjusting pH to 5-7 and adjusting the concentration of rebamipide to 0.5-5% (w/v), and filtrating the mixture for sterilization.

The other inventions are definite through the following description.

The aqueous suspension containing crystalline rebamipide of the invention can foe prepared by mixing at least one of the compounds selected from water-soluble polymers and surfactants, an aqueous acidic solution, and an aqueous solution containing a water-soluble salt of rebamipide, and crystallizing the crystalline rebamipide. Furthermore, the aqueous ophthalmic suspension containing crystalline rebamipide can be prepared by adjusting pH to 5-7 and adjusting the concentration of rebamipide to 0.5-5% (w/v).

The above-mentioned crystallisation of rebamipide may be carried out by (i) mixing an aqueous acidic solution containing at least one of the compounds selected from water-soluble polymers and surfactants, and an aqueous solution containing a water-soluble salt of rebamipide, or (ii) mixing an aqueous acidic solution and an aqueous solution containing a water-soluble salt, of rebamipide and at least one of the compounds selected from water-soluble polymers and surfactants, or (iii) mixing an aqueous acidic solution containing at least one of the compounds selected from water-soluble polymers and surfactants, and an aqueous solution containing a water-soluble salt of rebamipide and at least one of the compounds selected from the same water-soluble polymers and surfactants.

The acid used in the aqueous acidic solution of the invention can be a conventional acid such as hydrochloric acid, sulfuric acid, nitric acid, carbonic acid, phosphoric acid, citric acid, and the like, preferably hydrochloric acid.

The salt of rebamipide in the invention may be formed with a conventional base such as sodium hydroxide, potassium hydroxide, triethanoiamine, tromethanol(tris-[hydroxymethyl]aminomethane), meglumine, diethanolamine and the like, and the salt of sodium hydroxide which is a water-soluble salt is preferably used. Rebamipide can be used as the above salt form or as a free acid, provided that it should be used with an equimolar or more of the above, base when it is used as a free acid. The amount of the above-mentioned, acid is preferably at least the amount required to neutralize the above base. The method used for mixing the above solution preferably includes, but is not limited to, a mixing-procedure accompanied with shearing force, in a stirring/dispersing machine which is conventionally used for pharmaceutical formulation such as a disperser, a homomixer, and a homogeniser. Additionally, the method may include a exposure to ultrasonic wave at the mixing process.

The water-soluble polymer or surfactant of the invention includes, for example, polyvinyl alcohol, hydroxypropyl cellulose, hydroxyethyl cellulose, methyl cellulose, hydroxypropylmethyl cellulose, polyvinyl-pyrrolidone, polyethylene glycol (Macrogoi), polysorbate 80, sodium carboxymethyl cellulose, earhoxyvinyl polymer, water-soluble chitosan, sodium chondroitin sulfate, sodium alginate, polyoxyethylene-polyoxypropylene glycol (e.g., polyoxyethylene[160]polyoxypropylene[30]glycol, polyoxyethylene[196]polyoxypropylene[67]glycol), polyoxyethylene hydrogenated castor oil 40, polyoxyethylene hydrogenated castor oil 60, polyoxy 40 stearate and the like.

Among the above examples, hydroxypropylmethyl cellulose, polyvinyl-pyrrolidone, and polyoxyethylene-polyoxypropylene glycol are preferable, and more preferred are hydroxypropylmethyl cellulose and polyvirryl-pyrrolidone, especially hydroxypropylmethyl cellulose.

The methoxyl content and the hydroxypropoxyl content of the hydroxypropylmethyl cellulose used in the Invention are preferably 19-30% and 4-12%, more preferably 28-30% and 7-12%, respectively. The viscosity grade of hydroxypropylmethyl cellulose (2% (w/v) aqueous solution) is preferably less than 50 mm$^2$/s, more preferably not more than 15 mm$^2$/s, even more preferably 6 mm$^2$/s. The added concentration of hydroxypropylmethyl cellulose in the prepared suspension is preferably 0.1-10% (w/v), more preferably 0.5-5% (w/v), even more preferably 1-3% (w/v). The concentration ratio between rebamipide and hydroxypropylmethyl cellulose is preferably 20:1-1:20, more preferably 2:1-1:6.

The molecular weight of the polyvinyl-pyrrolidone of the invention is preferably not more than 200,000, more preferably not more than 40,000. The added concentration of polyvinylpyrrolidone in the prepared suspension, is preferably 0.1-10% (w/v) more preferably 0.3-5% (w/v), even more preferably 0.5-3% (w/v). The concentration ratio between rebamipide and polyvinyl-pyrrolidone is preferably 20:1-1:20, more preferably 4:1-1:6.

The polyoxyethylene-polyoxypropylene glycol used in the invention includes polyoxy ethylene [160]polyoxypropylene[30]glycol and polyoxyethylene[196]polyoxypropylene[67]glycol. The added amount of polyoxyethylene-polyoxypropylene glycol or polysorbate 80 in the prepared suspension is preferably 0.001%-1% (w/v), more preferably 0.01%-0.1% (w/v).

In addition, the combination of hydroxypropylmethyl cellulose and polysorbate 80 or polyoxyethylene-polyoxypropylene glycol, and the combination of polyvinyl-pyrrolidone and polysorbate 80 or polyoxyethylene-polyoxypropylene glycol are preferably employed.

The present inventors have also found that the re-dispersibility and transparency of the aqueous suspension is further enhanced by adding a base to the aqueous suspension containing crystalline rebamipide prepared by the crystallization as mentioned above to adjust pH to 3-7, and then stirring and dispersing the mixture.

The base used herein may be the same as the aforementioned base.

The stirring and dispersing machines used herein are conventional stirring and dispersing machines used for pharmaceutical formulation such as a disperser, a homomixer, and a homogenizer, preferably a stirring and a dispersing machine which makes "agglomerated particles in the liquid" effectively-dispersed. The preferable examples include a rotary homogenizer such as ROBOMICS® (TOKUSHU KIKA KOGYO CO., LTD) and CLEARMIX®, a wet-type jet mill and a high-pressure homogenizer. In particular, in using CLEAKMIX® W-MOTION (M-TECHNIQUE CO., LTD.) wherein a screen and a rotor are counter-rotated at high speed to give a strong liquid-liquid shearing force, the transparency of the aqueous suspension containing crystalline rebamipide as prepared above is remarked enhanced. Especially, an aqueous suspension of crystalline rebamipide together with hydroxypropylmethyl cellulose, as an additive exhibits a surprisingly high transparency.

The present inventors have found that the transparency is further enhanced by additionally dialyzing (i.e., diafiitration) the aqueous suspension of crystalline rebamipide prepared by the above crystallisation.

The dialysis machines used herein include conventional dialysis machines used for pharmaceutical formulation such as Pellicon® (Millipore Japan), Prostak® (Millipore Japan), and Sartocon® (Sartorius). During the dialytic process, when the pH of an aqueous suspension containing crystalline rebamipide is low, the flow on dialytic membrane is low due to the agglomeration; while when the pH is high, the rebamipide is dissolved and hereby the content is decreased. Therefore, it is desirable that the dialysis procedure is carried out in the suspension at pH of 3-7, preferably pH of 4-7, more preferably pH of 5-7.

An aqueous suspension of crystalline rebamipide together with hydroxypropylmethyl cellulose as an additive exhibits a surprisingly high transparency when desalted with a dialysis machine. Thereby, it has become possible to formulate a suspension suitable for a stable eye drop whose aspect is unchanged under even enhanced temperature.

The above dialyzing process and dispersing/stirring process may be carried out alone at each process or in combination; or the dispersing/stirring process may be carried out after the dialyzing process; or reversely the dialysing process may be carried out after the dispersing/stirring process.

The suspension is concentrated through the dialyzing process, and hence the suspension of crystalline rebamipide at any concentration between 0.1% (w/v) and 10% (w/v), preferably between 0.5% (w/v) and 5% (w/v), can be prepared by diluting the concentrated suspension with purified water.

Furthermore, the present inventors have found that the crystal shape of rebamipide in the suspension is controlled by the above method and the aspect of the resultant suspension is improved through the method.

The crystalline rebamipide in the suspension, having a long gage length of less than 1000 nm and a short gage length of less than 60 nm, provided that the ratio between the long gage length and the short gage length is not less than 4, may be preferably given.

For example, when polyvinyl-pyrrolidone is used as an additive, a suspension of a regular needle crystal can be prepared through the above preparing process, which has a long gage length of less than 300 nm and a short gage length of less than 60 nm, preferably a long gage length of about 200 nm and a short gage length of about 40 nm, provided that the ratio between the long gage length and the short gage length of about 5. And the suspension exhibits a preferable dispersibility and a good filterability through 0.2 μm filter. Furthermore, for example, when hydroxypropylmethyl cellulose is used as an additive, a regular hyperneedle crystal can be prepared through the above preparing process, which has a long gage length of less than 1000 nm and a short gage length of less than 30 nm, preferably a long gage length of not less than 50 nm to less than 1000 nm and a short gage length of 5-20 nm, provided that the ratio between the long gage length and the short gage length is more than 7. And when the suspension is put in combination of dispersing process and dialysing process, the suspension which has a very high transparency and can pass through 0.2 μm filter can be given.

For example, the suspension of crystalline rebamipide as prepared above may contain sodium chloride which is prepared by a neutralization of hydrochloric acid and sodium hydroxide, which makes it possible to prepare an ophthalmic suspension exhibiting an osmotic pressure of approximately 1. When the suspension is hypotonic due to the dialyzing process or other; sodium chloride, potassium chloride, mannitol, glycerin, sorbitol, and/or glucose, particularly preferably glycerin, which are generally used in eye drop, are used in order to make it isotonic with lacrimal fluid.

The pH of the formulation is adjusted to 5-7 by adding a pH regulator such as an acid, e.g. hydrochloric acid, sulfuric acid, nitric acid, carbonic acid, phosphoric acid, and citric acid; or a base, e.g. sodium hydroxide, potassium hydroxide, triethanol amine, tromethanol (tris[hydroxymethyl]aminomethane), meglumine, and diethanolamine, so that the irritation at eye can be lower.

In addition, various additives which are generally used in eye drop such as buffer, preservative (antiseptic), stabilizer and the like, may be further added to the formulation.

The examples of the buffer include acetic acid and acetate salt such as sodium acetate, citric acid and citrate salt; phosphate salt such as sodium dihydrogen phosphate, disodium hydrogen phosphate, potassium, dihydrogen phosphate, dipotassium hydrogen phosphate and the like; amino acid salt such as ε-aminocaproic acid, sodium glutamate and the like; boric acid and borate salt.

The examples of the preservative include quaternary ammonium salts such as benzalkonium chloride, benzethonium chloride and the like; cation compounds such as chlorohexidine gluconate and the like; p-oxybenzoate esters such as methyl p-oxybenzoate, propyl p-oxybenzoate and the like; alcohol compounds such as chlorobutanol, benzyl alcohol and the like; sodium dehydroacatate, thimerosal; and the like.

The examples of the stabilizer include ascorbic acid and salt, thereof, tocopherol, sodium thiosulfate, sodium hydrogen sulfite, sodium edetate and the like.

The ophthalmic suspension of the invention may be also provided as a unit dose type (preservative-free type) which is not contaminated by microorganism.

It is noted that it had been so far impossible to prepare an aqueous ophthalmic suspension comprising rebamipide, which does not need to be re-dispersed and exhibit a remarkable transparency. However, firstly an aqueous suspension of crystalline rebamipide exhibiting pH of 1-3 is given by mixing at least one of the compounds selected from water-soluble polymers and surfactants, an aqueous acidic solution such as hydrochloric acid, and an aqueous solution containing a water-soluble salt of rebamipide; and next, to the said suspension a base is added to adjust the pH; and then the mixture is stirred/dispersed and desalted through the process of dialysis; and finally it has become possible, to prepare an aqueous ophthalmic suspension containing rebamipide as an active ingredient, which is neutral to weakly acidic and is not necessary to be re-dispersed, has an advantageous transparency and stability. According to the method of the invention, it has been possible to sterilize the suspension through a sterile filtration and hence it is a great industrial advantage at the viewpoint that the aseptic active ingredient is not necessary. In addition, the aqueous ophthalmic suspension of rebamipide prepared by the method of the invention has become possible to be sufficiently stable as a pharmaceutical product.

The ophthalmic suspension of the invention may get rid of blurred vision or uncomfortableness of a patient, and hence it will be expectable that a patient suffering from dry eye is really acceptant of the suspension, and the invention may provide enormous contribution on the medical field.

BEST MODE FOR CARRYING OUT THE INVENTION

Figure 1:
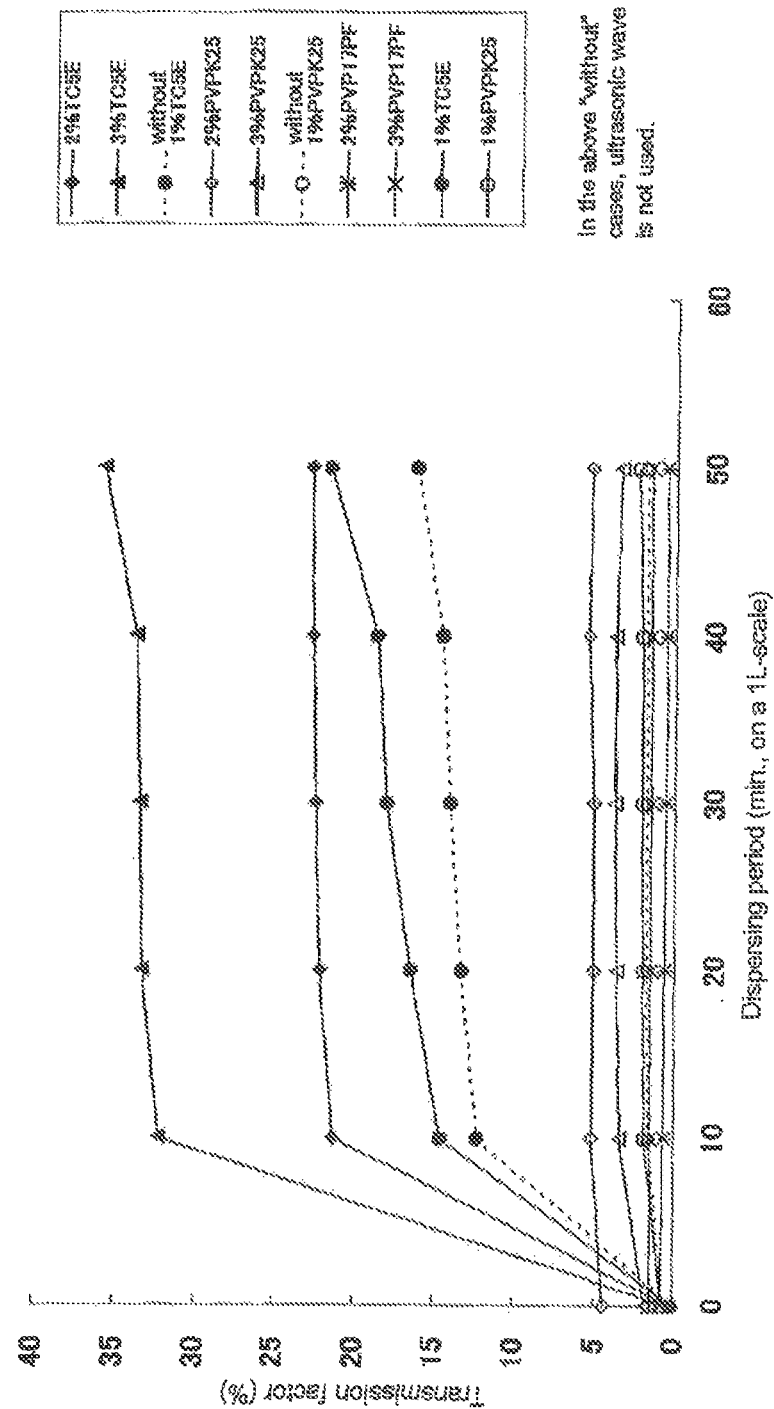
FIG. 1 shows each transmission factor of the original solutions after the CLEARMIX® dispersion.

Hereinafter, the present invention is further illustrated by the following examples, but should not be construed to be limited thereto.

The following abbreviations employed in the examples are as follows:

Hydroxypropylmethyl cellulose (HPMC, Shin-Etsu Chemical Co., LTD, Grade: TC-5E): HPMC (TC-5E) or TC-5E.

Polyvinyl-pyrrolidone (PVP, BASF, Grade: Kollidon® 25): PVP (K-25).

Polyvinyl-pyrrolidone (PVP, BASF, Grade: Kollidon® 17PF); PVP (K-17PF).

Polyoxyethylene[160]polyoxypropylene[30]glycol (Pluronic® F68 [PF68], BASF, Grade: Lutrol F68): Pluronic® F68 or PF68.

Polyoxyethylene[196]polyoxypropylene[67]glycol (Pluronic® F127, Asahi Denka. Co., LTD.); Pluronic® F127 or PF127.

Example 1

1 L of an aqueous suspension including 2% (w/v) crystalline rebamipide was prepared by the following procedure.

12 ML of 10 N hydrochloric acid (14.2 g, 0.12 mol), 68 mL of purified water, and 200 mL of an aqueous solution containing some of the additives listed in Table 1 (the concentration of the additives is 5 fold of that, in the desired suspension product that will be prepared) were mixed to prepare a hydrochloric acid-additives solution. To 700 mL of an aqueous solution of sodium hydroxide which was prepared by adding purified water to 4.4 g of sodium hydroxide (0.11 mol), 20 g of rebamipide (0.054 mol) was added and dissolved with heating to give a sodium hydroxide-rebamipide solution.

The hydrochloric acid-additives solution at ice temperature was exposed to ultrasonic wave with an Ultrasonic Disrupter (TGMY UD201) stirring at the speed of 1400 rpm with a disperser (ROBOMICS®, TOKUSHU KIKA KOGYO CO., LTD). The sodium hydroxide-rebamlpicle solution kept at 30-40° C. was added to the hydrochloric acid-additives solution by small and small to deposit crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH between 6.0 and 6.5. The desired aqueous suspension containing 2% (w/v) crystalline rebamipide and the additives was prepared by getting the volume of the liquid to 1 L. The suspension includes approximately 0.7% (w/v) of sodium chloride (approximately 0.12 mol) which was given by the neutralization of the hydrochloric acid and the sodium hydroxide.

Example 2

800 ML of the aqueous suspension containing 2% (w/v) crystalline rebamipide, which was prepared by the procedure of Example 1, was stirred at 10,000 rpm for 10 minutes with a disperser (ROBOMICS®, TOKUSHU KIKA KOGYO CO., LTD).

Evaluation of Examples 1 and 2

The particle sizes of the suspensions before and after the dispersing procedure were measured with a Laser Diffraction Particle Size Distribution Analyzer (SALD 3000J, Shimadzu Corporation). The particle size which is measured in a circulatory cell for analysis under ultrasonic wave, using 0.2% (w/v) HPC-SL solution as a dispersion medium, is called "primary particle size"; while the particle size which is measured in a batch cell for analysis without ultrasonic wave, using purified water as a dispersion medium, is called "secondary particle size". The both particle sizes were measured. The secondary particle size shows the agglutinability of the suspension more potently in comparison with the primary particle size. In order to evaluate the transparency of the samples, the 2% (w/v) suspension was diluted 10-fold with purified water (to 0.2% (w/v) solution), and the transmission factor of the diluted solution was measured at 640 nm with a spectrophotometer (Shimadzu Recording spectrophotometer, UV-240).

The results are shown in Table 1. The primary particle size of the additive-free solution containing the re-crystals was 1 μm, and the secondary particle size, was about 7 μm. When 1% (w/v) HPMC (TC-5E) was added to the additive-free solution containing the re-crystals and the mixture was dispersed by a ROBOMICS®, then the primary particle size decreased to 0.3 μm and the secondary, particle size decreased to 0.6 μm. From these results, it has been clarified that the particles in the solution containing the re-crystals were agglutinated.

The suspension containing the re-crystallized rebamipide, to which an aqueous polymer or a surfactant was added, exhibited a marked enhancement of the transparency in the 10-fold diluting solution (0.2% (w/v) solution) in comparison, with the case of the additive-free solution. Furthermore, the primary particle size of the suspension containing an aqueous polymer or a surfactant, after dispersed by a ROBOMICS®, became smaller than that of the additive-free suspension.

TABLE 1

Evaluation of the aqueous suspension containing 2% (w/v) rebamipide in Examples 1 and 2

| Additives* | Suspension after crystallization (Before dispersion by a ROBOMICS ®, Example 1) | | | Suspension after dispersion with a ROBOMICS ® (Example 2) | | |
| --- | --- | --- | --- | --- | --- | --- |
| | Primary particle size (μm) | Secondary particle size (μm) | Transmission factor of 10-fold diluted solution (%) | Primary particle size (μm) | Secondary particle size (μm) | Transmission factor of 10-fold diluted solution (%) |
| None** | 1.0 | 6.7 | 0.1 | 0.34 | 0.62 | 0.1 |
| Pluronic ® F68 | 0.17 | 0.39 | 23.8 | 0.19 | 0.37 | 24.3 |
| HPMC (TC-5E) | 8.7 | 20.3 | 5.1 | 0.20 | 29.0 | 63.9 |
| TC-5E + 0.01% w/v polysorbate 80 | 0.15 | 1.9 | 51.9 | 0.13 | 0.34 | 61.8 |
| TC-5E + 0.01% w/v Pluronic ® F68 | 0.16 | 20.4 | 33.4 | 0.15 | 0.38 | 61.5 |
| TC-5E + 0.01% w/v Pluronic ® F127 | 0.18 | 0.39 | 60.5 | 0.20 | 0.31 | 63.0 |
| PVP (K25) | 3.8 | 45.8 | 25.5 | 0.21 | 0.86 | 34.4 |
| PVP(K25) + 0.01% w/v polysorbate 80 | 0.19 | 0.15 | 51.9 | 0.13 | 0.44 | 39.9 |
| PVP(K25) + 0.01% w/v Pluronic ® F68 | 0.19 | 0.21 | 43.9 | 0.19 | 0.20 | 45.2 |
| PVP(K25) + 0.01% w/v Pluronic ®F127 | 0.19 | 0.21 | 37.0 | 0.19 | 0.28 | 37.4 |

*When the concentration of the above additive is not denoted on the above table, it means that the concentration is 1% (w/v) after preparing the suspension.
**To only suspension without any additives dispersed by ROBOMICS ®, 1% (w/v) HPMC (TC-5E) was added and then the mixture was dispersed by ROBOMICS ®.

Example 3

800 ML of the aqueous suspension containing 2% (w/v) rebamipide, which was prepared by the procedure of Example 1, was dispersed for 30 minutes with a CLEARMIX® W-MOTION (M-TECHNIQUE CO., LTD.) wherein the rotor was turned at about 17,000 rpm and the screen was turned at about 16,000 rpm. The average particle size of the dispersed suspension was measured with a Dynamic Light Scattering Particle Size Analyzer (Microtrac UFA and Otsuka Electronics Co., Ltd. ELS-8000). The solution prepared by 10-fold dilating the 2% (w/v) suspension with purified water (0.2% (w/v) solution), and the original 2% (w/v) suspension were measured at 640 nm with a spectrophotometer (Shimadzu Recording spectrophotometer, UV-240) to give the transmission factors, and the results are shown in Table 2. When using a CLEARMIX® W-MOTION (M-TECHNIQUE CO., LTD.) for the dispersion, the particle size of the suspension became smaller and the transmission factor markedly increased, in comparison with the case of the suspension dispersed at 10,000 rpm using a ROBOMICS®. In addition, the dispersed suspension has become possible to be filtrated through 0.2 μm filter.

TABLE 2

| Analytical item/additive | 1% (w/v) HPMC (TC-5E) | 1% (w/v) PVPK 25 | 1% (w/v) TC-5E + 0.01% (w/v) PF68 | 1% (w/v) PVPK 25 + 0.01% (w/v) PF68 |
| --- | --- | --- | --- | --- |
| Average cumulant particle size of ELS8000 (nm) | 135.6 | 111.9 | 133.9 | 113.8 |
| 50% D of Microtrc (UPA) (nm) | 77.4 | 96.3 | 92.8 | 93.0 |
| Transmission factor at 640 nm of 10-fold diluted solution (%) | 78.0 | 50.7 | 71.2 | 49.8 |
| Transmission factor at 640 nm of the original solution (%) | 19.7 | 0.4 | 7.7 | 0.3 |
| Filterability through 0.22 μm 25φ Millipore GV (PVDF) filter | 5 cc | 5 cc | Hardly penetrated | 1 cc |
| Filterability through 0.8/0.2 μm 32φ Pall Supor filter | Easily penetrated | Easily penetrated | Easily penetrated | Easily penetrated |

Example 4

1-4 L of an aqueous suspension containing 2% (w/v) rebamipide was crystallised according to the procedure of Example 1. The amount of each material was arranged by calculating in proportion to the amount of 1 L preparation. Also, a suspension without the treatment of ultrasonic wave during the process of crystallisation was prepared. The resultant aqueous suspension including 2% (w/v) rebamipide was dispersed with a CLEARMIX® W-MOTION (M-TECHNIQUE CO., LTD.) wherein the rotor was turned at about 18,000 rpm and the screen was turned at about 16,000 rpm. The average particle size of the dispersed suspension (Z-Average size) was measured with a Dynamic Light Scattering Particle Size Analyser (Malvern Nano-ZS). The solution prepared by 10-fold diluting the 2% (w/v) suspension with purified water (0.2% (w/v) solution), and the original 2% (w/v) suspension were measured with a spectrophotometer (Shimadzu Recording Spectrophotometer, (UV-240) to obtain the transmission factor at 640 nm, and the results are shown in Table 3 and FIG. 1.

The product to which HPMC (TC-5E) was added during the crystallizing procedure exhibited an increase of the transparency and an improvement of the filterability when it was exposed to ultrasonic wave during the crystallisation. The transmission factor at 640 nm increased in proportion to the concentration of HPMC (TC-5E) added within the range of 1-3% (w/v).

TABLE 3

Evaluation of the aqueous suspension containing 2% (w/v) rebamipide in Examples 4

| Additive | Exposed to ultrasonic wave | Batch volume at crystallizing | Batch volume at dispersing | Dispersing time (min) | Average particle size (nm) | Transmission factor at 640 nm (%) The original solution | 10-Fold diluted solution | Filterability through 0.2 μm |
|---|---|---|---|---|---|---|---|---|
| 1% w/v TC-5E | No | 1.5 L | 1 L | 50 | 105.5 | 16.2 | 76.0 | A little poor |
| 1% w/v TC-5E | Yes | 4 L | 3 L | 150 | 95.2 | 21.6 | 79.6 | Good |
| 2% w/v TC-5E | Yes | 1.5 L | 1 L | 50 | 108.5 | 22.7 | 78.2 | Good |
| 3% w/v TC-5E | Yes | 1.5 L | 1 L | 50 | 103.8 | 35.7 | 85.1 | Good |
| 1% w/v PVPK 25 | No | 1.5 L | 1 L | 50 | 88.8 | 1.8 | 62.1 | Very good |
| 1% w/v PVPK 25 | Yes | 4 L | 3 L | 150 | 88.7 | 2.4 | 65.1 | Very good |
| 2% w/v PVPK 25 | Yes | 1.5 L | 1 L | 50 | 87.0 | 5.3 | 70.3 | Very good |
| 3% w/v PVPK 25 | Yes | 1.5 L | 1 L | 50 | 90.4 | 3.4 | 65.2 | Very good |
| 2% PVP 17PF | Yes | 1.5 L | 1 L | 50 | 96.4 | 0.6 | 54.7 | A little poor |
| 3% PVP 17PF | Yes | 1.5 L | 1 L | 50 | 90.1 | 1.6 | 61.0 | A little poor |

Example 5

According to the procedure of Example 4, the sample containing 1% (w/v) HPMC (TC-5E) as an additive, which was prepared by dispersing with a CLEARMIX®, was concentrated and desalted by a dialysis machine (Millipore, Pellicon® XL50). After the dialysis, to the resultant solution, purified water was added to prepare 2% (w/v) rebamipide suspension again. With respect to the suspensions before and after dialysis, the average particle sizes (Z-Average sizes) of them were measured with a Dynamic Light Scattering Particle Size Analyzer (Malvern Nano-ZS), the transmission factors at 640 nm of the 2% (w/v) suspensions were measured with a spectrophotometer, and the results are shown in Table 4.

When desalted with a dialysis, the particle size became smaller and the transmission factor thereof markedly increased contrary to our expectation.

TABLE 4

The average particle size and the transmission factor at 640 nm of the 2% (w/v) rebamipide suspensions before and after dialysis (including 1% (w/v) HPMC [TC-5E])

| Dialysis | Average particle size (nm) | Transmission factor at 640 nm of 2% w/v suspension (%) |
|---|---|---|
| before | 126 | 16.2 |
| after | 104 | 45.0 |

Example 6

12 ML of 10 N hydrochloric acid (14.2 g, 0.12 mol), 68 mL of purified water, and 200 mL of an aqueous solution of 5% (w/v) HPMC (TC-5E) were mixed to prepare a hydrochloric acid-HPMC (TC-5E) solution. To 700 mL of an aqueous solution of sodium hydroxide which was prepared by adding purified water to 4.4 g of sodium, hydroxide (0.11 mol), 20 g of rebamipide (0.054 mol) was added and dissolved with heating to give a sodium hydroxide-rebaxaipide solution.

The hydrochloric acid-additives solution at ice temperature was exposed to ultrasonic wave with an Ultrasonic Disrupter (TOMY UD201) stirring at the speed of 1400 rpm with a disperser (ROBOMICS®, TOKUSHU KIKA KOGYO CO., LTD). The sodium hydroxide-rebamipide solution kept at 30-40° C. was added to the hydrochloric acid-additives solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium, hydroxide was added to adjust pH to about 5.0.

The resultant aqueous suspension containing rebamipide was dispersed for 30 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, Pellicon® 2 mini).

An isotonic agent-free sample and a sample containing glycerin as an isotonic agent were prepared from the concentrated and desalted sample. And purified water was added to each of the samples to give 2 kinds of 2% (w/v) rebamipide suspensions.

(1) 2% (w/v) rebamipide+1% (w/v) HPMC (TC-5E)
(2) 2% (w/v) rebamipide+1% (w/v) HPMC (TC-5E)+2.5% (w/v) glycerin Each of these samples was divided into 3 solutions and they were stored at 4° C., 60° C., and under a cycle condition (at 4° C. for 12 hours; at 40° C. for 12 hours; repeatedly). And the average particle sizes (Z-Average sizes) of them were measured with a Dynamic Light Scattering Particle Size Analyzer (Malvern Nano-ZS), the transmission factors at 640 nm of these 2% (w/v) suspensions were measured with a spectrophotometer, and the results are shown in Table 5.

According to the desalting with, dialysis, it became possible that the enlargement of the particle size of the stored samples and the decrease of the transmission factor are markedly depressed. Additionally, it also became possible to depress the gelation caused by the storage at 60° C. and under the cycle condition.

When adding a nonionic isotonic agent, the enlargement of the particle size and the decrease of the transmission factor tended to be depressed.

TION (M-TECHNIQUE CO., LTD.) wherein the rotor was turned at about 18,000 rpm and the screen was turned at about 16,000 rpm, and then the solution was concentrated and desalted with a dialysis machine (Millipore, Pellicon® 2 mini).

An isotonic agent-free sample and a sample containing glycerin as an isotonic agent were prepared from the concentrated and desalted sample. Purified water was added to each of the samples to give 2 kinds of 2% (w/v) rebamipide suspensions.
(1) 2% (w/v) rebamipide+1% (w/v) PVPK 25
(2) 2% (w/v) rebamipide+1% (w/v) PVPK 25+2.4% (w/v) glycerin Example 8

12 ML of 10 N hydrochloric acid (14.2 g, 0.12 mol), 68 mL of purified water, and 200 mL of an aqueous solution of 5% (w/v) PVPK 25 were mixed to prepare, a hydrochloric acid-PVPK 25 solution. To 700 mL of an aqueous solution of sodium hydroxide which was prepared by adding purified water to 4.4 g of sodium hydroxide (0.11 mol), 20 g of rebamipide (0.054 mol) was added and dissolved with heating to give a sodium hydroxide-rebamipide solution.

TABLE 5

Time-dependent change of average particle size and transmission factor at 640 nm of 2% (w/v) rebamipide suspension (including 1% (w/v) HPMC [TC-5E])

|  | Dialysis | Isotonic agent | Average particle size (nm) | | Transmission factor of the original solution (%) | | Aspect after 2 weeks |
|---|---|---|---|---|---|---|---|
|  |  |  | 1 week later | 2 weeks later | 1 week later | 2 weeks later |  |
| Storage at 4° C. | No | No | 165 | 177 | 11.6 | 11.2 | Unchanged |
|  | Yes | No | 123 | 125 | 32.3 | 30.5 | Unchanged |
|  | Yes | glycerin | 125 | 125 | 33.1 | 30.7 | Unchanged |
| Storage at 60° C. | No | No | 402 | 459 | 4.9 | 4.0 | Gelated |
|  | Yes | No | 201 | 213 | 14.8 | 13.4 | Unchanged |
|  | Yes | glycerin | 186 | 202 | 16.9 | 15.6 | Unchanged |
| Storage under the cycle condition | No | No | 283 | 311 | 5.5 | 5.0 | Partly gelated |
|  | Yes | No | 148 | 172 | 21.4 | 17.1 | Unchanged |
|  | Yes | glycerin | 145 | 168 | 22.2 | 18.2 | Unchanged |

Average particle size (nm) at starting time
Before dialysis: 158 nm, After dialysis: 122 nm Example 7

12 ML of 10 N hydrochloric acid (14.2 g, 0.12 mol), 68 mL of purified water, and 200 mL of an aqueous solution of 5% (w/v) PVPK 25 were mixed to prepare a hydrochloric acid-PVPK 25 solution. To 700 mL of an aqueous solution of sodium hydroxide which was prepared by adding purified water to 4.4 g of sodium hydroxide (0.11 mol), 20 g of rebamipide (0.054 mol) was added and dissolved with heating to give a sodium hydroxide-rebamipide solution.

The hydrochloric acid-additives solution at ice temperature was exposed to ultrasonic wave with an Ultrasonic Disrupter (TOMY UD201) stirring at the speed of 1400 rpm with a disperser (ROBOMICS®, TOKUSHU KIKA KOGYO CO., LTD). The sodium hydroxide-rebamipide solution kept at 30-40° C. was added to the hydrochloric acid-additives solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH to about 5.0.

The resultant aqueous suspension containing rebamipide was dispersed for 30 minutes with a CLEARMIX® W-MO- The hydrochloric acid-additives solution at ice temperature was exposed to ultrasonic wave with an Ultrasonic Disrupter (TOMY UD201) stirring at the speed of 1400 rpm with a disperser (ROBOMICS®, TOKUSHU KIKA KOGYO CO., LTD). The sodium hydroxide-rebamipide solution kept at 30-40° C. was added to the hydrochloric acid-additives solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH to about 5.0.

The solution was concentrated and desalted with a dialysis machine (Millipore, Pellicon® 2 mini). After dialyzing, purified water was added thereto so that the volume of the solution was recovered to about 900 mL. The resultant aqueous suspension containing rebamipide was dispersed for 30 minutes with a CLEARMIX® W-MOTION (M-TECHNIQUE CO., LTD.) wherein the rotor was turned at about 18,000 rpm and the screen was turned at about 16,000 rpm.

An isotonic agent-free sample and a sample containing glycerin as an isotonic agent were prepared from the dispersed sample. Purified water was added to each of the samples to give 2 kinds of 2% (w/v) rebamipide suspensions.
(1) 2% (w/v) rebamipide+1% (w/v) PVPK 25
(2) 2% (w/v) rebamipide+1% (w/v) PVPK 25+2.4% (w/v) glycerin The prepared samples were filtrated for sterilization through 0.2 μm filter (Supor®, Nihon Pall Ltd.).

Example 9

24 ML of 10 N hydrochloric acid (28.4 g, 0.24 mol), 136 mL of purified water, and 400 mL of an aqueous solution containing 10% (w/v) HPMC (TC-5E) were mixed to prepare a hydrochloric acid-HPMC (TC-5E) solution. To 1400 mL of an aqueous solution of sodium hydroxide which was prepared by adding purified water to 8.8 g of sodium hydroxide (0.22 mol), 40 g of rebamipide (0.108 mol) was added and dissolved, with heating to give a sodium hydroxide-rebamipide solution.

The hydrochloric acid-additives solution at ice temperature was exposed to ultrasonic wave with an Ultrasonic Disrupter (TOMY UD201) stirring at the speed of 1400 rpm with a disperser (ROBOMICS®, TOKUSHU KIKA KOGYO CO., LTD). The sodium, hydroxide-rebamipide solution kept at 30-40° C. was added to the hydrochloric acid-additives solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH to about 5.0.

The resultant aqueous suspension including rebamipide was dispersed for 30 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, Pellicon® 2 mini).

An isotonic agent-free sample and a sample containing glycerin as an isotonic agent were prepared from the concentrated and desalted sample. Sodium hydroxide solution was added to each of the samples to adjust pH of the solution to 6.0, and then purified water was added for the adjustment of the total amount to prepare 2 kinds of 2% (w/v) rebamipide suspensions.
(1) 2% (w/v) rebamipide+2% (w/v) HPMC [TC-5E]
(2) 2% (w/v) rebamipide+2% (w/v) HPMC [TC-5E]+2.35% (w/v) glycerin The prepared samples were filtrated for sterilization through 0.22 μm filter (STERIVEX® GP 0.22 μm Filter, Millipore Japan).

Example 10

12 Ml of 10 N hydrochloric acid (14.2 g, 0.12 mol), 68 mL of purified water, and 200 mL of a mixture of 2.5% (w/v) PVPK 25+2.5% (w/v) HPMC (TC-5E) were mixed to prepare a hydrochloric acid-HPMC (TC-5E)-PVPK 25 solution. To 700 mL of an aqueous solution of sodium hydroxide which was prepared by adding purified water to 4.4 g of sodium hydroxide (0.11 mol), 20 g of rebamipide (0.054 mol) was added and dissolved with heating to give a sodium hydroxide-rebamipide solution.

The hydrochloric acid-additives solution at ice temperature was exposed to ultrasonic wave with an Ultrasonic Disrupter (TOMY UD201) stirring at the speed of 1400 rpm with a disperser (ROBOMICS®, TOKUSHU KIKA KOGYO CO., LTD). The sodium hydroxide-rebamipide solution kept at 30-40° C. was added to the hydrochloric acid-additives solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH to about 5.0.

The resultant aqueous suspension containing rebamipide was dispersed for 30 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, Pellicon® 2 mini).

An isotonic agent-free sample and a sample containing glycerin as an isotonic agent were prepared from the concentrated and desalted sample. Purified water was added to each of the samples to give 2 kinds of 2% (w/v) rebamipide suspensions.
(1) 2% (w/v) rebamipide+0.5% (w/v) PVPK 25+0.5% (w/v) HPMC HPMC [TC-5E]
(2) 2% (w/v) rebamipide+0.5% (w/v) PVPK 25+0.5% (w/v) HPMC [TC-5E]+2.4% (w/v) glycerin The prepared samples were filtrated for sterilisation through 0.22 μm filter (STERIVEX® GP 0.22 μm Filter, Millipore Japan).

Example 11

24 ML of 10 N hydrochloric acid (28.4 g, 0.24 mol), 136 ml, of purified water, and 400 mL of an aqueous solution including 3% (w/v) HPMC (TC-5E) were mixed to prepare a hydrochloric acid-HPMC (TC-5E) solution. To 1400 mL of an aqueous solution of sodium hydroxide which was prepared by adding 8.8 g of sodium hydroxide (0.22 mol) and 23 g of HPMC (TC-5E) to purified water, 40 g of rebamipide (0.108 mol) was added and dissolved with heating to give a sodium hydroxide-rebamipide-HPMC (TC-5E) solution.

The hydrochloric acid-HPMC (TC-5E) solution at ice temperature was stirred at the speed of 1400 rpm with a disperser (ROBOMICS®, TOKUSHU KIKA KOGYO CO., LTD). The sodium hydroxide-rebamipide-HPMC (TC-5E) solution kept at 30-40° C. was added to the hydrochloric acid-HPMC (TC-5E) solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH to 5.5.

The resultant aqueous suspension containing rebamipide was dispersed for 30 minutes with a CLEARMIX® W-MOTION (M-TECHNIQUE CO., LTD.) wherein the rotor was turned at about 18,000 rpm and the screen was turned at about 16,000 rpm. Then, the solution was concentrated and desalted with a dialysis machine (Millipore, Pellicon® 2 mini).

Glycerin was added to the residue so that the concentrated and desalted sample became almost isotonic. Sodium hydroxide solution was added thereto to adjust pH of the solution to 6.0, and then purified water was added for the adjustment of the total amount to prepare a 2% (w/v) rebamipide suspension.

2% (w/v) rebamipide+2% (w/v) HPMC [TC-5E]+2.35% (w/v) glycerin

The prepared samples were, filtrated for sterilization through 0.22 μm filter (STERIVEX® GP 0.22 μm Filter, Millipore Japan).

Example 12

24 ML of 10 N hydrochloric acid (28.4 g, 0.24 mol) and 536 mL of purified water were mixed to prepare a hydrochloric acid solution. To 1400 mL of an aqueous solution of sodium hydroxide which was prepared by adding 8.8 g of sodium hydroxide (0.22 mol) and 40 g of HPMC (TC-5E) to purified water, 40 g of rebamipide (0.108 mol) was added and dissolved with heating to give a sodium hydroxide-rebamipide-HPMC (TC-5E) solution.

The hydrochloric acid solution at ice temperature was stirred at the speed of 1400 rpm with a disperse (ROBOMICS®, TOKUSHU KIKA KOGYO CO., LTD). The sodium hydroxide-rebamipide-HPMC (TC-5E) solution kept at 30-40° C. was added to the hydrochloric acid solution by small and small to deposit a crystalline rebamipide. After the crystal was deposited, the stirring speed was raised to 3000 rpm and the stirring was continued for 20 minutes. After completing the crystallization, the pH of the solution was about 1.5. The solution was defoamed, and then to the defoamed solution, 5 N sodium hydroxide was added to adjust pH to 6.0.

The resultant, aqueous suspension containing rebamipide was dispersed for 30 minutes with a CLEARMIX® W-MOTION (M-TECHNIQUE CO., LTD.) wherein the rotor was turned at about 18,000 rpm and the screen was turned at about 16,000 rpm. Then, the solution was concentrated and desalted, with a dialysis machine (Millipore, Pellicon® 2 mini).

Glycerin was added to the residue so that the concentrated and desalted, sample became almost isotonic. Hydrochloric acid or sodium hydroxide solution was added thereto to adjust the pH of the solution to 6.0, and then purified water was added for the adjustment of the total amount to prepare a 2% (w/v) rebamipide suspension.

2% (w/v) rebamipide+2% (w/v) HPMC [TC-5E]+2.35% (w/v) glycerin

The prepared samples were filtrated for sterilization through 0.22 μm filter (STERIVEX® GP 0.22 μm Filter, Millipore Japan).

Example 13

366 ML of 10 N hydrochloric acid (432 g, 3.66 mol) and 7.8 L of an aqueous solution containing 7.67% (w/v) HPMC (TC-5E) were mixed to prepare a hydrochloric acid-HPMC (TC-5E) solution. To 21 L of an aqueous solution of sodium hydroxide which was prepared by adding purified water to 132 g of sodium hydroxide (3.3 mol), 600 g of rebamipide (1.62 mol) was added and dissolved with heating to give a sodium hydroxide-rebamipide solution.

The hydrochloric acid-HPMC (TC-5E) solution cooled at about 10° C. was allowed to circulate in a 350 mL vessel equipped with a disperser (CLEARMIX® S-MOTION, M-TECHNIQUE CO., LTD.) as an in-line type. The sodium hydroxide-rebamipide solution kept at 40-50° C. was thrown by small and small to the 350 mL vessel with a CLEARMIX® S-MOTION wherein the rotor was turned at about 1,500 rpm to deposit a crystalline rebamipide. After completing the crystallization, the pH of the solution was about 1.5. To the crystal-deposited solution, 5 N sodium hydroxide was added to adjust pH to about 5.75.

1 L of the resultant aqueous suspension containing rebamipide was dispersed for 30 minutes with a CLEARMIX® W-MOTION (M-TECHNIQUE CO., LTD.) wherein the rotor was turned at about 18,000 rpm and the screen was turned at about 16,000 rpm and then the solution was concentrated and desalted with a dialysis machine (Millipore, Pellicon® 2 mini).

The sample given from the above concentrating and desalting was diluted with purified water to prepare a 2% (w/v) rebamipide suspension (2% (w/v) rebamipide+2% (w/v) HPMC [TC-5E]).

The transmission factor at 640 nm of the given suspension was measured, and the average particle size (Z-Average size) thereof was measured with a Dynamic Light Scattering Particle Size Analyzer (Malvern Nano-ZS).

TABLE 6

The average particle size and the transmission factor at 640 nm of the 2% (w/v) rebamipide suspension

| Average particle size (nm) | Transmission factor at 640 nm of 2% (w/v) suspension (%) |
| --- | --- |
| 92.5 | 50.4 |

Example 14

373 ML of 10 N hydrochloric acid (440 g, 3.73 mol) and 14.8 L of an aqueous solution containing 4% (w/v) HPMC (TC-5E) were mixed to prepare a hydrochloric acid-HPMC (TC-5E) solution. To 14 L of an aqueous solution of sodium hydroxide which was prepared by adding purified water to 134 g of sodium hydroxide (3.35 mol), 600 g of rebamipide (1.62 mol) was added and dissolved with heating to give a sodium hydroxide-rebamipide solution.

The hydrochloric acid-HPMC (TC-5E) solution cooled at about 10° C. the sodium hydroxide-rebamipide solution kept at 50-60° C. was thrown at the same additional rate to the 350 mL vessel with a dispenser (CLEARMIX® S-MOTION, M-TECHNIQUE CO., LTD.) wherein the rotor was turned at about 10,000 rpm to give a suspension containing a crystalline rebamipide. After completing the crystallization, the pH of the solution was about 1.5. To the crystal-deposited solution, 5 N sodium hydroxide was added to adjust pH to about 5.75.

3 L of the resultant aqueous suspension containing rebamipide was dispersed for 60 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, ProFlux® M12).

The sample given from the above concentrating and desalting was diluted with purified water to prepare a 2% (w/v) rebamipide suspension (2% (w/v) rebamipide+2% (w/v) HPMC [TC-5E]).

The transmission factor of the given suspension at 640 nm was measured, and the average particle size (Z-Average size) thereof was measured with a Dynamic Light Scattering Particle Size Analyzer (Malvern Nano-ZS).

TABLE 7

The average particle size and the transmission
factor at 640 nm of the 2% (w/v) rebamipide suspension

| Average particle size (nm) | Transmission factor at 640 nm of 2% (w/v) suspension (%) |
|---|---|
| 104.2 | 62.5 |

Example 15

61 ML of 10 N hydrochloric acid (72 g, 0.61 mol) and 1.3 L of an aqueous solution containing 7.67% (w/v) HPMC (TC-5E) were mixed to prepare a hydrochloric acid-HPMC (TC-5E) solution. To 3.5 L of an aqueous solution of sodium hydroxide which was prepared by adding purified water to 22 g of sodium hydroxide (0.55 mol), 100 g of rebamipide (0.27 mol) was added and dissolved with heating to give a sodium hydroxide-rebamipide solution.

The hydrochloric acid-HPMC (TC-5E) solution cooled at about 10° C. was allowed to circulate in a 350 mL vessel equipped with a disperser (CLEARMIX® S-MOTION, M-TECHNIQUE CO., LTD.) as an in-line type. The sodium hydroxide-rebamipide solution kept at 40-50° C. was thrown by small and small to the 350 mL vessel with a CLEARMIX® S-MOTION wherein the rotor was turned at about 12,000 rpm to deposit a crystalline rebamipide. After completing the crystallization, the pH of the solution was about 1.5. To the crystal-deposited solution, 5 N sodium hydroxide was added to adjust pH to about 5.75.

3 L of the resultant aqueous suspension containing rebamipide was dispersed for 60 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, ProFlux® M12).

The sample given from the above concentrating and desalting was diluted with purified water to prepare a 2% (w/v) rebamipide suspension (2% (w/v) rebamipide+2% (w/v) HPMC [TC-5E]).

The transmission factor at 640 nm of the given suspension was measured, and the average particle size (Z-Average size) thereof was measured with a Dynamic Light Scattering Particle Size Analyzer (Malvern Nano-ZS).

TABLE 8

The average particle size and the transmission
factor at 640 nm of the 2% (w/v) rebamipide suspension

| Average particle size (nm) | Transmission factor at 640 nm of 2% (w/v) suspension (%) |
|---|---|
| 91.2 | 80.0 |

Example 16

183 ML of 10 N hydrochloric acid (216 g, 1.83 mol) and 3.9 L of an aqueous solution containing 7.67% (w/v) HPMC (TC-5E) were mixed to prepare a hydrochloric acid-HPMC (TC-5E) solution. To 10.5 L of an aqueous solution of sodium hydroxide which was prepared by adding purified water to 66 g of sodium hydroxide (1.65 mol), 300 g of rebamipide (0.81 mol) was added and dissolved with heating to give a sodium hydroxide-rebamipide solution.

The hydrochloric acid-HPMC (TC-5E) solution cooled at about 10° C. was allowed to circulate in a silicon block whose inside was an L-shaped cavity. The sodium hydroxide-rebamipide solution kept at 40-50° C. was thrown by small and small into the block to deposit crystalline rebamipide. After completing the crystallisation, the pH of the solution was about 1.5. To the crystal-deposited solution, 5 N sodium hydroxide was added to adjust pH to about 5.75.

3 L of the resultant aqueous suspension containing rebamipide was dispersed for 60 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, ProFlux® M12).

The sample given from the above concentrating and desalting was diluted with purified water to prepare a 2% (w/v) rebamipide suspension (2% (w/v) rebamipide+2% (w/v) HPMC [TC-5E]).

The transmission factor at 640 nm of the given suspension was measured, and the average particle size (Z-Average size) thereof was measured with a Dynamic Light Scattering Particle Size Analyzer (Malvern Nano-ZS).

TABLE 9

The average particle size and the transmission
factor at 640 nm of the 2% (w/v) rebamipide suspension

| Average particle size (nm) | Transmission factor at 640 nm of 2% (w/v) suspension (%) |
|---|---|
| 110.7 | 62.7 |

Test 1

The samples of above Example 6 (1) and Example 7 (1) were ultra-centrifuged by a Beckman L7-Ultracentrifuge (50,000 rpm, for 60 minutes, 10° C.) to precipitate fine-grain. After washing it with purified water, the same operation was carried out again. The supernatant was removed and the resultant precipitate was air-dried for 4 days at 4° C.

X-ray diffraction, spectra, IR spectra and DTA-TG spectra of the dried fine-grain were measured. The spectra of the dried fine-grain was the same as that of the active ingredient which was prepared in the second plant of OTSUKA PHARMACEUTICAL CO., LTD, and has been used for treating gastric ulcer and gastritis. These results indicate that the fine-grained crystal given in the invention has the same crystal shape as the ordinary active ingredient useful for treating gastric ulcer and gastritis.

Test 2

Figure 2:
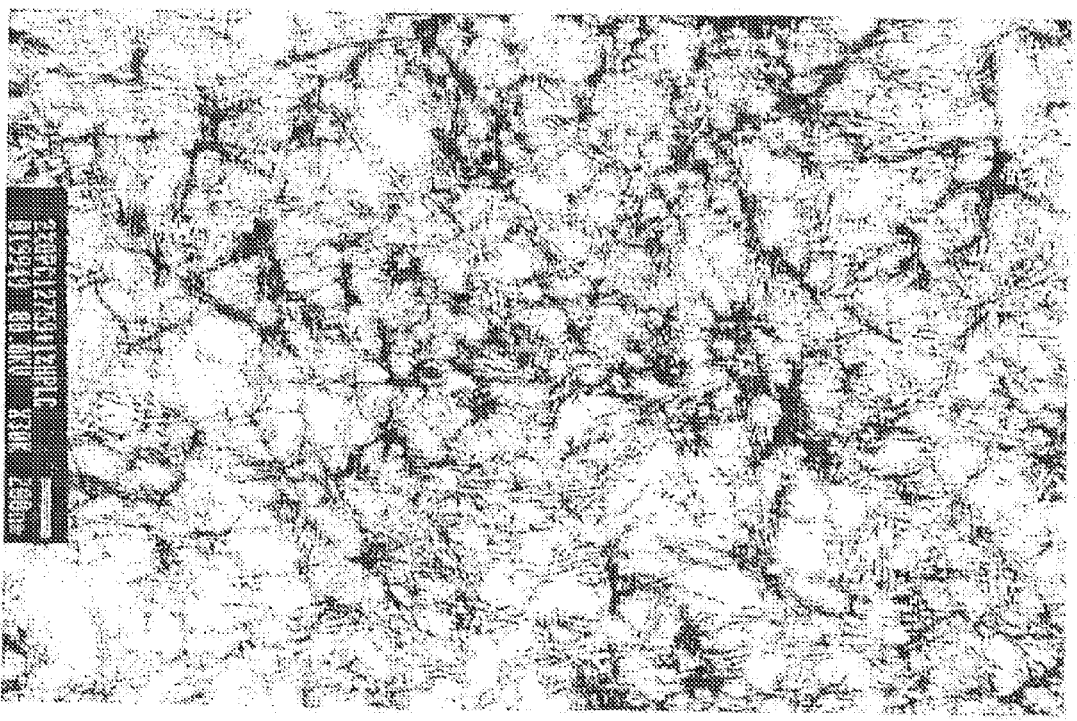
FIG. 2 shows the shape of the crystalline rebamipide from 2% (w/v) rebamipide+1% (w/v) HPMC [TC-5E] shown in Example 6 (1) through a transmission electron microscope.
Figure 3:
FIG. 3 shows the shape of the crystalline rebamipide from 2% (w/v) rebamipide+1% (w/v) PVPK 25 shown in Example 7 (1) through a transmission electron microscope.

The crystal shapes of the samples of above Example 6 (1) and Example 7 (1) were measured with a transmission electron microscope (FIG. 2, FIG. 3). When watching 2% (w/v) rebamipide+1% (w/v) HPMC [TC-5E] in above Example 6 (1) with a transmission electron microscope, the crystal shape of the resultant crystal was a regular hyper-needle crystal having a long gage length of not less than 300 nm to less than 1000 nm, a short gage length of about 15 nm, provided that the ratio between the long gage length and the short gage length is more than 20. When such hyper-needle crystal was given, it was presumed that the obtained suspension could have a high transparency.

When watching 2% (w/v) rebamipide+1% (w/v) PVPK 25 in Example 7 (1) with a transmission electron microscope, the crystal shape of the resultant crystal was a regular needle crystal having a long gage length of about 200 nm, a short gage length of about 40 nm, provided that the ratio between the long gage length and the short gage length is about 5. When such hyper-needle crystal was given, it was presumed that, the obtained suspension could have a high dispensability and a good filterability through 0.2 μm filter.

Test 3

Figure 4:
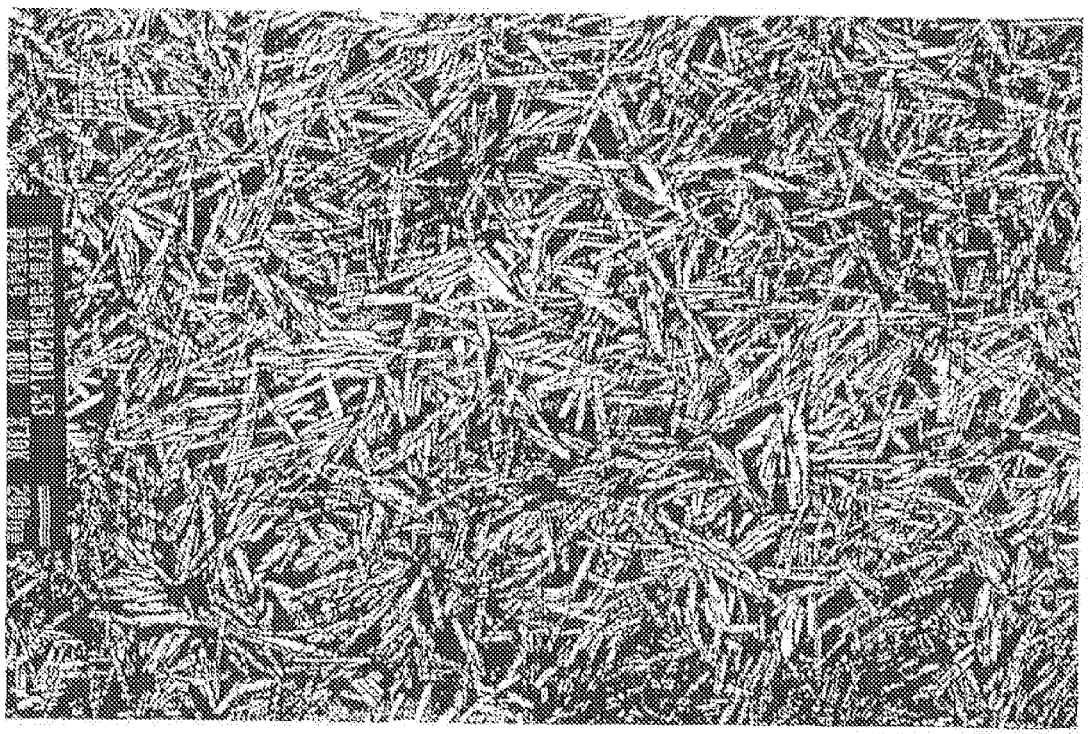
FIG. 4 shows the shape of the crystalline rebamipide from 2% (w/v) rebamipide+2% (w/v) HPMC [TC-5E] shown in Example 13 through a transmission electron microscope.

The crystal shape of the sample of above Example 13 was measured with a transmission electron microscope (FIG. 4). When watching 2% (w/v) rebamipide+2% (w/v) HPMC [TC-5E] in above Example 13 with a transmission electron microscope, the crystal shape of the resultant crystal was a regular hyper-needle crystal having a long gage length of not less than 50 nm to less than 400 nm, a short gage length of about 15 nm, provided that the ratio between the long gage length and the short gage length is more than 8. When such hyper-needle crystal was given, it was presumed that the obtained suspension could have a high transparency and a good filterability to 0.2 μm filter.

The invention claimed is:

1. A process of preparing an aqueous suspension of crystalline rebamipide comprising (1) a water-soluble salt of rebamipide; (2) hydroxypropylmethyl cellulose (HPMC) or polyvinylpyrrolidone (PVP); (3) hydrochloric acid; and (4) water; comprising:
   (a) mixing an aqueous solution comprising a polymer selected from HPMC or PVP with hydrochloric acid and purified water to form a hydrochloric acid-HPMC/PVP solution;
   (b) dissolving rebamipide in an aqueous solution comprising NaOH to form a sodium hydroxide-rebamipide solution;
   (c) adding the sodium hydroxide-rebamipide solution of step (b) to the hydrochloric acid-HPMC/PVP solution step (a) to deposit crystalline rebamipide;
   (d) stirring the suspension of step (c) to complete the crystallization; and
   (e) adjusting the pH of the aqueous suspension of step (d) to 5-7 with sodium hydroxide;
   wherein the shape of crystalline rebamipide is a regular crystal having a long gage length of less than 1000 nm and a short gage length of less than 60 nm, provided that the ratio between the long gage length and short gage length is not less than 4.

2. The process according to claim 1 wherein in the mixing process the mixture is subjected to exposure of ultrasonic wave.

3. The process according to claim 1 wherein the suspension contains hydroxypropylmethyl cellulose.

4. The process of preparing an aqueous suspension of crystalline rebamipide comprising (1) a water-soluable salt of rebamipide; (2) hydroxypropylmethyl cellulose (HPMC) or polyvinylpyrrolidone (PVP); (3) hydrochloric acid; and (4) water; comprising:
   (A) mixing
      (a) an aqueous acidic solution containing Ingredient (2) and Ingredient (3), and
      (b) an aqueous solution containing Ingredient (1),
   (B) mixing
      (a) an aqueous acidic solution containing Ingredient (3), and
      (b) an aqueous solution containing Ingredient (2) and Ingredient (1), or
   (C) mixing
      (a) an aqueous acidic solution containing Ingredient (2) and Ingredient (3), and
      (b) an aqueous solution containing Ingredient (2) and Ingredient (1) to prepare an aqueous suspension exhibiting pH of 1-3,
   adding a base to the aqueous suspension to adjust the pH to 3-7,
   dispersing and/or dialyzing the mixture, and then adjusting the pH of the mixture to 5-7 with a base and
   adjusting the concentration of rebamipide to 0.5-5% (w/v).

5. The process of preparing an aqueous suspension of crystalline rebamipide comprising (1) a water-soluable salt of rebamipide; (2) hydroxypropylmethyl cellulose (HPMC) or polyvinylpyrrolidone (PVP); (3) hydrochloric acid; and (4) water; comprising:
   (A) mixing
      (a) an aqueous acidic solution containing Ingredient (2) and Ingredient (3), and
      (b) an aqueous solution containing Ingredient (1),
   (B) mixing
      (a) an aqueous acidic solution containing Ingredient (3), and
      (b) an aqueous solution containing Ingredient (2) and Ingredient (1), or
   (C) mixing
      (a) an aqueous acidic solution containing Ingredient (2) and Ingredient (3), and
      (b) an aqueous solution containing Ingredient (2) and Ingredient (1) to prepare an
   aqueous suspension exhibiting pH of 1-3,
   adding a base to the aqueous suspension to adjust the pH to 3-7,
   dispersing and/or dialyzing the mixture, then
   adjusting the pH of the mixture to 5-7 with a base and
   adjusting the concentration of rebamipide to 0.5-5% (w/v), and
   filtrating the mixture for sterilization.

6. The process according to claim 5 wherein the concentration of rebamipide in the suspension concentrated by the dialysis is adjusted to 0.5-5% (w/v) with purified water.

7. The process according to claim 5 wherein the aqueous suspension of crystalline rebamipide having a concentration of 0.5-5% (w/v) has a transmission factor at 640 nm of not less than 20%.

8. The process according to claim 1, wherein the acidic range for the aqueous suspension of crystalline rebamipide prepared by the mixing process is pH of 1-3.

* * * * *

UNITED STATES PATENT AND TRADEMARK OFFICE
CERTIFICATE OF CORRECTION

PATENT NO. : 9,533,052 B2  
APPLICATION NO. : 14/887222  
DATED : January 3, 2017  
INVENTOR(S) : Takakuni Matsuda et al.

Page 1 of 1

It is certified that error appears in the above-identified patent and that said Letters Patent is hereby corrected as shown below:

On the Title Page

In the Abstract, Item (57), Line 3, "so weakly" should read as --to weakly--.

In the Abstract, Item (57), Line 3-4, "pH not to injury" should read as --pH so as not to injure--.

In the Claims

In Claim 2, Column 21, Lines 44-45, "exposure of ultrasonic wave" should read as --exposure to ultrasonic wave--.

Signed and Sealed this  
Eighteenth Day of April, 2017

Michelle K. Lee  
*Director of the United States Patent and Trademark Office*